United States Patent [19]

Massaro et al.

[11] Patent Number: 5,433,883
[45] Date of Patent: Jul. 18, 1995

[54] TOILET BAR COMPOSITIONS COMPRISING NONIONIC GLYCOLIPID SURFACTANTS AND POLYALKYLENE GLYCOL STRUCTURANT

[75] Inventors: Michael Massaro, Congers, N.Y.; George Grudev, Hewitt; Gail B. Rattinger, Teaneck, both of N.J.

[73] Assignee: Lever Brothers Company, Division of Conopco, Inc., New York, N.Y.

[21] Appl. No.: 148,120

[22] Filed: Nov. 4, 1993

[51] Int. Cl.⁶ .......................... C11D 9/00; C11D 9/30
[52] U.S. Cl. .................... 252/174.17; 252/108; 252/117; 252/542; 252/548; 252/DIG. 16
[58] Field of Search ............... 252/108, 117, 542, 548, 252/DIG. 16, 174.17

[56] References Cited

U.S. PATENT DOCUMENTS

| | | | |
|---|---|---|---|
| 2,752,334 | 6/1956 | Walton | 260/211 |
| 3,312,627 | 4/1987 | Hooker | 252/152 |
| 5,037,973 | 8/1991 | Meinetsberger | 536/53 |
| 5,069,808 | 12/1991 | Gerling et al. | 252/99 |
| 5,296,588 | 3/1994 | Au et al. | 536/1.11 |

FOREIGN PATENT DOCUMENTS

| | | | |
|---|---|---|---|
| 0550281 | 7/1993 | European Pat. Off. | A61K 7/50 |
| 2523962 | 3/1982 | France | C07C 103/34 |

*Primary Examiner*—Paul Lieberman
*Assistant Examiner*—Patricia Hailey
*Attorney, Agent, or Firm*—Ronald A. Koatz

[57] ABSTRACT

The present invention relates to toilet bar compositions comprising aldobionamides and an amount of polyalkylene glycol sufficient to structure the bar. Unexpectedly it has been found that this polyalkylene glycol structures the bar without simultaneously inhibiting lather formation.

8 Claims, No Drawings

TOILET BAR COMPOSITIONS COMPRISING NONIONIC GLYCOLIPID SURFACTANTS AND POLYALKYLENE GLYCOL STRUCTURANT

BACKGROUND OF THE INVENTION

The present invention relates to toilet bar compositions comprising nonionic glycolipid surfactants, more specifically the invention relates to nonionic aldobionamides in combination with sufficient amount of polyalkylene glycol to act as a structurant without simultaneously inhibiting lather formation.

Soap is an efficient cleaning surfactant which has been used historically in toilet bar compositions. Because soap can be harsh on the skin, however, for many years it has been sought to find a milder (i.e., less harsh) surfactant which can be used together with or in place of soap in such toilet bar compositions. U.S. Pat. No. 4,695,395 to Caswell et al. for example, teaches a toilet bar composition comprising both soap and acyl fatty isethionate and which composition is substantially milder to the skin then pure soap.

Another goal of the art has been to utilize mild, non-soap surfactants which are prepared from natural, biodegradable materials such as, for example saccharides. Applicants' parent application, U.S. Ser. No. 981,739, for example, teaches the use of aldobionamides as surfactants, for example, in toilet bar compositions.

In non-soap detergent active bars, it is the free fatty acid which acts to structure the bar (i.e., keep it from physically falling apart). Thus, in a bar based entirely on aldobionamide active, for example, a certain minimum level of fatty acid (i.e., 5–30% by weight, preferably 15 to 25% by weight) is generally required to structure the bar.

While aldobionamide is a mild biodegradable surfactant, it has been found that the bar does not have good lather characteristics, at least when used with a fatty acid structurant. Since lather production is an important characteristic to many bar users, this is considered to be a strong negative.

U.S. Pat. No. 3,312,627 to Hooker discloses bar compositions containing 0 to 70% of a high molecular weight base component and 10% to 70% of a nonionic detergent surfactant. It is disclosed that the base polymer may be a polyglycol and that the nonionic may be stearoyl N-methyl glucamide (column 5, line 1)

It should be noted that the nonionic surfactant is a glucamide in contrast to the gluconamide of the invention. Glucamides are expected to be less soluble. This particular compound would be expected to be even less soluble in that it is a $C_{18}$ stearoyl compound. In addition there is absolutely no recognition that this particular combination of components should be used or that they would result in a bar having the characteristics of the bar of the invention.

Unexpectedly, applicants have now discovered that if a certain minimum level of polyalkylene glycol is used in the composition (i.e., a minimum level of about 15% by weight alkylene glycol), the polyalkylene glycol not only can be used to structure the non-soap surfactant bar in place of fatty acid, but the polyalkylene glycol also does not inhibit lather formation in an aldonamide bar.

While U.S. Ser. No. 981,739 identified above discloses that polyethylene glycol may be used as an optional ingredient in combination with aldobionamide (page 12, second paragraph), there is no teaching or suggestion that the polyethylene glycol should or could be used in structuring amounts (i.e., in amounts greater than the amount of free fatty acid used) or that the polyethylene glycol surprisingly does not inhibit lather production in an aldobionamide bar the way free fatty acid does. In fact when alkylene glycol is used, lather volumes rivaling those of a commercial anionic bar are obtained ant lather volumes are far in excess of those obtained in a lactobionamide/fatty acid bar.

BRIEF SUMMARY OF THE INVENTION

The present invention relates to toilet bar compositions comprising 20 to 75% by weight nonionic aldobionamide surfactant, preferably 30–60% by weight and 15 to 65% by weight, preferably 25–50% by weight polyalkylene glycol which both functions as a structurant and does not inhibit lather formation. The toilet bar compositions may additionally comprise soap or non-soap surfactant other than aldobionamide (i.e., anionic, nonionic or amphoteric surfactants). The soap or non-soap surfactants should be used in an amount no greater than the amount of aldobionamide, preferably from about 15 to 45% of the amount of aldobionamide. The bar also may contain, for example, dyes, perfumes, moisturizers, skin feel agents (e.g., silicone, cationic polymers, fluorinated compounds etc.) and other bar components such as are well known to those skilled in the art.

DETAILED DESCRIPTION OF THE INVENTION

The present invention relates to toilet bar compositions comprising environmentally friendly surfactants, in particular environmentally friendly nonionic surfactants, such as aldobionamides.

Aldobionamides are defined as the amide of an aldobionic acid (or aldobionolactone) and an aldobionic acid is a sugar substance (e.g., any cyclic sugar comprising at least two saccharide units) wherein the aldehyde group (generally found at the $C_1$ position of the sugar) has been replaced by a carboxylic acid, which upon drying cycles to an aldonolactone.

An aldobionamide may be based on compounds comprising two saccharide units (e.g., lactobionamides or maltobionamides from the aldobionamide bonds), or they may be based on compounds comprising more than two saccharide units, as long as the terminal sugar in the polysaccharide has an aldehyde group. By definition an aldobionamide must have at least two saccharide units and cannot be linear. Disaccharide compounds such as lactobionamides or maltobionamides are preferred compounds. Other examples of aldobionamides (disaccharides) which may be used include cellobionamides, melibionamides and gentiobionamides.

A specific example of an aldobionamide which may be used for purposes of the invention is the disaccharide lactobionamide set forth below:

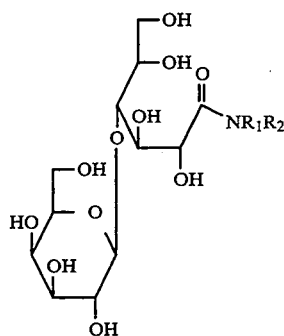

wherein $R_1$ and $R_2$ are the same or different and are selected from the group consisting of hydrogen; an aliphatic hydrocarbon radical (e.g., alkyl groups and alkene groups which groups may contain heteroatoms such as N, O or S or alkoxylated alkyl chains such as ethoxylated or propoxylated alkyl groups), preferably an alkyl group having 8 to 24, preferably 10 to 18 carbons; an aromatic radical (including substituted or unsubstituted aryl groups and areas); a cycloaliphatic radical; an amino acid ester, ether amines and mixtures thereof, except that $R_1$ and $R_2$ cannot be hydrogen at the same time.

Suitable aliphatic hydrocarbon radicals include saturated and unsaturated radicals including but not limited to methyl, ethyl, amyl, hexyl, heptyl, nonyl, decyl, undecyl, dodecyl, tridecyl, tetradecyl, pentadecyl, hexadecyl, heptadecyl, and octadecyl, and allyl, undecenyl, oleyl, linoleyl, linolenyl, propenyl, and heptenyl.

Aromatic radicals are exemplified, for example, by benzyl.

Suitable mixed aliphatic aromatic radicals are exemplified by benzyl, phenyl ethyl, and vinyl benzyl.

Cycloaliphatic radicals are exemplified by cyclopentyl and cyclohexyl.

The aldobionamides used in the composition of the invention have been found to have properties (i.e., critical micelle concentrations; Krafft Point; foaming; detergency) indicating that they are equal to or better than other well known nonionic surfactants which are based on petrochemicals (e.g., alkoxylated surfactants from the Neodol TM series from Shell), thereby indicating that they can be a viable, environmentally friendly alternative to the use of more traditional nonionic surfactants. The aldobionamides also have lower Krafft points and greater solubility than the single saccharide linear counterpart.

While not wishing to be bound by theory, it is believed that the higher solubility of the aldobionamide is due to the sugar structure which prevents the close packing which occurs in linear monosaccharide aldonamides such as gluconamides. The greater number of hydroxyl groups also probably help to make the aldobionamides more soluble.

In addition, the surfactants of the invention may be used as cosurfactants with other nonionic surfactants or with other surfactants (e.g., cationic, anionic, zwitterionic, amphoteric) used in personal product or detergent formulations. These should be used in an amount no greater than the amount of aldobionamide in the composition.

COMPOSITIONS

The compositions of the invention are toilet bar compositions comprising the aldobionamide defined above and polyalkylene glycol.

In the toilet bar compositions of the invention, fatty acid soaps are replaced by aldobionamides. The aldobionamides are used in an amount 20-75%, preferably 30-60% by weight of the composition.

The second required ingredient of the invention is a polyalkylene glycol (e.g., polyethylene, polypropylene or polybutylene) compound used in an amount both to structure the bar. The molecular weight range of the polyalkylene glycol is from 1,000 to 20,000, preferably 2,000 to 15,000, most preferably 6,000 to 10,000. Typically the alkylene glycol will comprise 15-65%, preferably 25-50% by weight. Preferably the polyalkylene is polyethylene glycol.

In addition to the aldobionamide surfactant of the invention, the compositions may also contain a soap or non-soap detergent which is generally chosen from anionic (including soaps), nonionic, cationic, zwitterionic or amphoteric synthetic detergent materials or mixtures thereof. The composition may also, of course, contain aldobionamide and polyalkylene glycol without additional coactive.

The surfactants are all well known in the art and are described, for example, in U.S. Pat. Nos. 4,695,395 to Caswell et al. and U.S. Pat. No. 4,260,507 to Barrett, both of which are incorporated herein by reference into the subject application. The actives should be used in an amount no greater than the amount of aldobionamide and preferably should comprise 15-45% of the amount of aldobionamide.

A certain amount of free fatty acids of 8 to 22 carbons are also desirably incorporated (although in theory they need not be incorporated) into the bar compositions to act as superfatting agents, skin feel and creaminess enhancers, and/or structurants. If present, the free fatty acids should comprise between 1 and 15% by weight of the compositions, but should comprise no more than the amount of polyalkylene glycol present.

Other optional ingredients which may be present in toilet bar compositions are moisturizers such as glycerin, propylene glycol, sorbitol, ethoxylated or methoxylated ether of methyl glucose etc; water-soluble polymers such as collagens, modified cellulases (such as Polymer JR ®), guar gums and polyacrylates; sequestering agents such as citrate, and emollients such as silicones mineral oil, petrolatum, or fluorinated polyethers.

The invention is set forth in greater detail in the examples which follow below. These examples are merely to illustrate the invention and are not intended to be limiting in any way.

EXAMPLES

Although not necessarily the only way to prepare N-alkyl lactobionamides, some methods for their preparation are discussed below.

Methods for Preparation of N-Alkyl Lactobionamides

Synthesis of N-Alkyl Lactobionamides

N-alkyl lactobionamides were synthesized by the reaction of commercially available lactobiono-1, 5-lactone with various linear alkylamines either in anhydrous DMF, methanol, or neat as shown below:

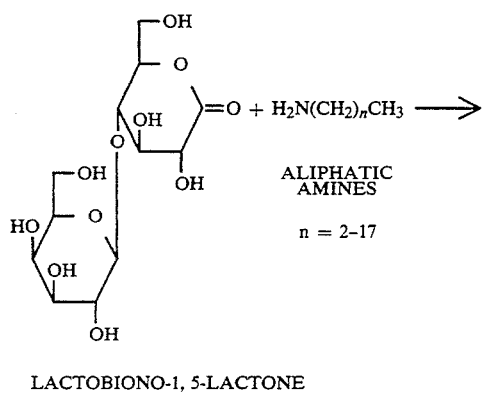

LACTOBIONO-1, 5-LACTONE

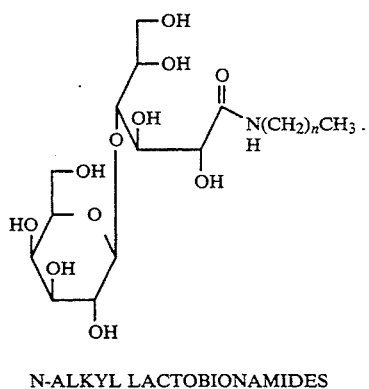

N-ALKYL LACTOBIONAMIDES

Dimethyl Formamide as Solvent

This procedure involved dissolving the lactobiono-1, 5-lactone in minimum amount of anhydrous DMF at 80° C. followed by the addition of 1 eq. of alkylamine. Although this procedure provided excellent yields, the products were colored and repeating washing with solvent was necessary.

Methanol as Solvent

This procedure was exercised as described in U.S. Pat. No. 2,752,334 to National Dairy. Lactobiono-1, 5-lactone and the alkylamines were refluxed in methanol and the corresponding colored products were isolated in moderate yields. Continuous washing with solvent was required for decoloration of the products.

Non-solvent Method

Excess alkylamines and lactobiono-1, 5-lactone were heated at 90°-100° with vigorous stirring. The colored products were isolated in moderate yields.

Examples of each of these methods is set forth in greater detail below:

Alternative Synthesis for N-tetadecyl Lactobionamide

In a 5 L three necked round bottom flask equipped with a condenser and mechanical stirrer, lactobiono-1, 5-lactone (400 g) was dissolved in warm methanol (3.5 L, 50°-55° C.). Melted tetradecylamine (1.0 eq, 272 g) was then added. The reaction was cooled to room temperature followed by stirring overnight to allow complete crystallization. The desired white product was filtered and recrystallized from methanol in 91% (550 g) isolated yield. The methanol filtrate contained a mixture of N-tetradecyl lactobionamide and tetradecylammonium lactonbionate.

The above procedure can also be used to isolate other N-alkyl aldonamides.

EXAMPLE 1

Preparation of N-decyl Lactobionamide 20 g of lactobiono-1, 5-lactone (1 eq) was dissolved in 40 ml of anhydrous DMF at 75°-80° C. with stirring for 30 minutes. The reaction was cooled, ethyl ether (150 ml) was added, the product was filtered and washed with ethyl ether (2×100 ml). Recrystallization from methanol/ethyl ether gave 80% yield of the desired product.

EXAMPLE 2

Preparation of N-dodecyl Lactobionamide 30 g of lactobiono-1, 5-lactone (1 eq) was dissolved in 70 ml of anhydrous DMF at 75°-80° C. 15.85 g (1 eq) dodecylamine was added, the reaction mixture was kept stirring at 70°-80° C. for 30 minutes. The reaction was allowed to cool, ethyl ether (200 ml) was added. The product was filtered and washed with ethyl ether (2×150 ml) and recrystallization from MeOH gave 90% of the desired product.

EXAMPLE 3

Preparation of N-tetradecyl Lactobionamide

Lactobiono-1 5-lactone (20 g, 1 eq) was dissolved in 60 ml of anhydrous DMF at 65° C. 12.5 g of tetradecylalmine (1 eq) was added, the reaction was stirred at 65° C. for 30 minutes. The reaction mixture was cooled-,ethyl ether (2×150 ml) was added. The product was filtered and washed with ethyl ether. Recrystallization from methanol yielded 92% of the desired product.

EXAMPLE 4

Preparation of N-hexadecyl Lactobionamide

The same procedure was employed as in Example 3 using 10 g of lactobiono-1,5-lactone (1 eq) and 7.1 g of hexadecylamine (1 eq). Recrystallization from MeOH yielded 90% of the desired product.

EXAMPLE 5

Preparation of N-propyl Lactobionamide 5 g of lactobiono-1, 5-lactone (1 eq) was dissolved in 20 ml of anhydrous DMF at 80° C. 0.86 g propylamine (1 eq) was added. The reaction was stirred at 80° C. for 30 minutes. The solvent was removed. The residue was washed with ethyl ether (2×50 ml). Recrystallization from MeOH/ethyl ether gave 80% yield of the desired product.

EXAMPLE 6

Preparation of N-pentyl Lactobionamide

Lactobiono-1, 5-lactone (5 g, 1 eq) and amylamine (1.41 g, 1 eq) was heated in 30 ml of anhydrous methanol to reflux for one hour. Small amount of activated charcoal was added, filtered when hot. The solvent was removed, the residue was washed with ethyl ether followed by acetone and dried. The yield was 50%.

EXAMPLE 7

Preparation of N-octyl Lactobionamide

Lactobiono-1, 5-lactone (10 g, 1 eq) and octylamine (7.6 g, 2 eq) was heated to 90° C. for 30 minutes with vigorous stirring. The reaction was allowed to cool, washed with (2×150 ml) of ethyl ether. Recrystallization twice from MeOH/ethyl ether gave 80% yield of the desired product.

EXAMPLE 8

Preparation of N-dodecyl Lactobionamide 20 g of lactobiono-1, 5-lactone and 11 g of dodecylamine (1 eq) was dissolved in 200 ml of methanol by heating it to reflux temperature. The reaction mixture was allowed to stir at room temperature overnight. The product was filtered, washed with methanol (100 ml), followed by ethyl ether (2×75 ml). Recrystallization from MeOH gave 57% yield of the desired product.

EXAMPLE 9

N-lactobionyl Dododecyl Glycinate 9.0 g of dodecyl glycinate hydrochloride as dissolved in 50 ml of anhydrous methanol by gentle heating, 16 ml of 2.0M methanolic ammonia was added,followed by addition of 10. g (1 eq) of lactobiono-1, 5,lactone. The reaction mixture was heated to reflux for 2.0 h and activated charcoal was added and the mixture was filtered hot. The solvent was removed, the product was washed with ethyl ether and dried in a vacuum oven at 40° C. with $P_2O_5$ to give a yield of approximately 75%.

EXAMPLE 10

N-lactobionyl Dodecyl B-alanate

The same procedure was employed as described above for the dodecyl glycinate form by reacting 3.0 g of dodecyl β-alanate hydrochloride with 3.45 of lactobiono-1, 5-lactone in anhydrous MeOH. The yield was approximately 70%.

EXAMPLE 11

N-decyloxypropyl Lactobionamide 50 g of lactobiono-1, 5-lactone was dissolved in 400 ml of methanol (50°–55° C.), decyloxypropylamine (Adogen ® 180, 31.6 g, 1 eq) was added. The reaction was cooled to room temperature followed by stirring overnight. The solvent was removed (250 ml) and acetone (400 ml) was added. The product was filtered, washed with acetone and dried in vacuum oven at 40° C. The yield was approximately 80%.

EXAMPLE 12

Preparation of Coco Lactobionamide

Lactobiono-1, 5-lactone (400 g, 1 eq) was dissolved in methanol (2.31, 50° C.) with stirring, cocoamine (Adogen 160-D ®, 211.8 g 1 eq) was added slowly over 10 minutes. After the addition was completed, the reaction mixture was stirred for an additional 10 minutes followed by seeding the solution with a small amount of coco lactobionamide and stirred overnight at room temperature. The product was filtered, washed with warm acetone twice and dried in a vacuum oven at 40° C. The yield was 394 g.

EXAMPLE 13

Preparation of Tallow Lactobionamide

Lactobiono-1, 5-lactone (200 g, 1 eq) was dissolved in methanol (45° C., 1.31) tallow amine (Adogen 170-D ®, 144.7 g, 1 eq) was added slowly in several portions. After the addition was completed, the reaction mixture was stirred overnight at room temperature. The product was filtered, washed with isopropanol followed by acetone and dried in a vacuum oven at 40° C. The yield was 270 g.

EXAMPLE 14

Preparation of Oleyl lactobionamide

Lactobiono-1, 5-lactone (100 g, 1 eq) was dissolved in methanol (50° C., 400 ml) oleylamine (Adogen 172-D ®, 76.1 g, 1 eq) was added slowly. After the addition was completed, the reaction was stirred at room temperature overnight. The product was filtered, washed with acetone 2× and dried in a vacuum oven at 40° C. The yield was 130 g.

EXAMPLE 15

Preparation of N-dodecyl-N-methyl Lactobionamide

Lactobiono-1, 5-lactone (8.7 g, 1 eq) was dissolved in methanol (50° C., 30 ml) N-dodecylmethylamine (55 g, 1 eq was added. The reaction was stirred overnight at room temperature. The solvent was removed, the product was washed with acetone and dried in a vacuum oven at 40° C. The yield was 12 g.

SURFACTANCY

In order to determine the effectiveness of the N-alkyl aldobionamide compounds as a surfactant, various physical properties (i.e., CMC, Krafft point, foam height, Zein dissolution, detergency) of the surfactant, which are associated with how "good" a surfactant is, were measured. In particular, these properties were compared to the well known and commonly used ethoxylated surfactants. The results of these various measurements are set forth in Example 16–19 below.

EXAMPLE 16

Critical Micelle Concentration (CMC)

The CMC is defined as the concentration of a surfactant at which it begins to form micelles in solution. Specifically materials that contain both a hydrophobic group and a hydrophilic group (such as surfactants) will tend to distort the structure of the solvent (i.e., water) they are in and therefore increase the free energy of the system. They therefore concentrate at the surface, where, by orienting so that their hydrophobic groups are directed away from the solvent, the free energy of the solution is minimized. Another means of minimizing the free energy can be achieved by the aggregation of these surface-active molecules into clusters or micelles with their hydrophobic groups directed toward the interior of the cluster and their hydrophilic groups directed toward the interior of the cluster and their hydrophilic groups directed toward the solvent.

The value of the CMC is determined by surface tension measurements using the Wilhemy plate method. While not wishing to be bound by theory, it is believed that a low CMC is a measure of surface activity (i.e., lower CMC of one surfactant versus another indicates the surfactant with lower CMC is more surface active). In this regard, it is believed that lower CMC signifies that lesser amounts of a surfactant are required to provide the same surfactancy benefits as a surfactant with higher CMC.

The CMC of various surfactants were measured and the results set forth below:

| Surfactant | CMC |
| --- | --- |
| n-Dodecyl-$\beta$-D-glucoside | $1.9 \times 10^{-4}$M (25° C.) |
| n-$C_{12}$ alcohol (with 7 EO's) | $7.3 \times 10^{-5}$M (40° C.) |
| $C_{10}$ lactobionamide | — |
| $C_{12}$ lactobionamide | $4.2 \times 10^{-4}$M (45° C.) |
| $C_{14}$ lactobionamide | $4.5 \times 10^{-5}$M (45° C.) |

As the table above indicates, the CMC values of N-decyl and tetradecyl lactobionamides were found to be comparable to that of N-Dodecyl-$\beta$-D glucoside and heptaethoxylateddodecyl alcohol. These values indicate that the lactobionamide surfactants are comparable to other widely used nonionic surfactants.

EXAMPLE 17

Krafft Points

The temperature at and above which surfactants begin to form micelles instead of precipitates is referred to as Krafft point (Tk) and at this temperature the solubility of a surfactant becomes equal to its CMC.

Krafft point was measured by preparing a 1% dispersion of the surfactant in water. If the surfactant was soluble at room temperature, the solution was cooled to 0° C. When the surfactant did not precipitate out, its Krafft point was considered to be <0° C. If it precipitated out, the solution was slowly warmed with stirring in a water bath. The temperature at which the precipitate dissolved was determined to be the Krafft point.

If the Krafft point was above room temperature, the solution was first heated rapidly to dissolve all t he surfactant. It was then cooled until precipitation occurred, and was then slowly warmed to determine the Krafft point described above.

While not wishing to be bound by theory, it is believed that lower Krafft points are indicative of a surfactant being more soluble in aqueous system.

The Krafft point of various lactobionamides is set forth as follows:

| | Kraft Point |
| --- | --- |
| $C_{10}$ - lactobionamide | 0° C. |
| $C_{12}$ - lactobionamide | 38° C. |
| $C_{14}$ - lactobionamide | 46° C. |

This table indicates that the $C_{10}$ chain length surfactants would tend to have better surfactancy properties than $C_{12}$ and $C_{14}$ counterparts at lower temperatures.

EXAMPLE 18

Foam Height

Foam is an important attribute in many consumer products (e.g., consumer products). Foam is one of the dominant factors that determines the commercial value of products such as shampoo, soap, etc. Also, acceptability of many consumer products is closely related to the quality and texture of the foam they produce (psychological aspect).

Since most of the foaming data on surfactants is typically obtained by the Ross-Miles method (Ross, J. and Miles, G. D. Am. Soc. for Testing Material method D1173-53 Philadelphia, Pa. (1953); Oil & Soap (1958) 62:1260) the foaming ability of these surfactants was also acquired using this method.

In the Ross-Miles method, 200 mL of a solution of surfactant contained in a pipette of specified dimensions with a 2.9-mm-i.d. orifice is allowed to fall 90 cm onto 50 mL of the same solution contained in a cylindrical vessel maintained at a given temperature (often 60° C.) by means of a water jacket. The height of the foam produced in the cylindrical vessel is read immediately after all the solution has run out of the pipette (initial foam height) and then again after a given amount of time (generally, 5 min).

Using this method, the foam production (measured initially) and foam stability (the height after 10 minutes) are reported. All of the foaming was achieved at 45° C. in water with 120 ppm hardness. The foam height is represented in millimeters (mm).

The initial foam height and height after 10 minutes (i.e., foam stability) for various surfactants and mixtures of surfactants is set forth below:

| | Initial Height | After 10 Minutes |
| --- | --- | --- |
| $C_{10}$ lactobionamide | 150 | 5 |
| $C_{12}$ lactobionamide | 153 | 20 |
| $C_{14}$ factobionamide | 145 | 140 |
| Mixture of $C_{12}$ and $C_{14}$ | 155 | 135 |
| Neodol 91-6 ($C_9$-$C_{11}$ alcohol plus 6 EO) | 130 | 5 |

As seen above, the $C_{14}$ lactobionamide and the mixture of $C_{12}$ and $C_{14}$ lactobionamides shows best form stability.

It should be noted that it is very unusual to get this type of foam stability with other nonionics.

EXAMPLE 19 & 20

Compositions 19 and 20 below were prepared as follows:

A mixer was heated to 100°-110° C. and PEG, fatty acid, and coactive (if present) were added and melted to a fluid, yet homogeneous, mixture. Next, the lactobionamide was added slowly to the mixer forming a thick dough. Water was added along with titanium dioxide and preservatives to thin the dough. The mixer temperature at this point was lowered so that a batch temperature of 85°-90° C. was achieved. During mixing, an extra 2-3% (weight %) water was typically added to ensure the dough was well mixed. When the batch dried to target moisture (~5%), it was discharged as a white, and fluffy dough.

The following compositions were prepared as described above

Example 19—Lactobionamide/PEG/Free Fatty Acid

| Ingredient | Wt. % |
| --- | --- |
| coco lactobionamide | 55.00 |
| palmitic-stearic acid | 6.97 |
| PEG 8000 | 27.80 |
| water | 5.00 |
| misc. solids (for example salts or other derivatives of lactobionic acid) | 4.23 |
| titanium dioxide | 0.50 |
| fragrance | 0.50 |
| Total | 100.00 |

*PEG 8,000 is polyethylene glycol having molecular weight of 8,000

Example 20—Lacobionamide/PEG/Free Fatty Acid/Fatty Acid Isethionate

| Ingredient | Wt. % |
|---|---|
| coco lactobionamide | 40.00 |
| sodium cocoyl isethionate | 15.00 |
| palmitic-stearic acid | 7.04 |
| PEG 8000 | 29.35 |
| water | 5.00 |
| misc. solids | 3.08 |
| sodium isethionate | 0.53 |
| Total | 100.00 |

EXAMPLE 21

In order to show that lactobionamide bars structured with polyalkylene glycol (i.e., bars containing at least 15% alkylene glycol and less than 15% free fatty acid) were mild (by virtue of their mild nonionic lactobionamide), and structured (by virtue of alkylene glycol structurant) and yet were able to maintain strong lathering characteristics, applicants compared the lathering properties of bars defined according to the invention with a typical anionic based syndet bar (i.e., a bar which lathers well by virtue of its anionic surfactant and in which the free fatty acid structurant does not depress lather formation as it does in the bar using primarily lactobionamide as a surfactant).

Specifically, applicants compared the lather volumes of the bars from example 19 and 20, respectively with the lather volumes generated by a typical anionic, free fatty acid structured bar.

Lather volume was determined as follows:

With a gloved hand, bar and glove are wetted and the bar is turned ten times under a stream of water (95° F.) to generate lather. The lather is pulled from both hands, ten times total, to accumulate a measurable volume and then gathered under an inverted cone which tapers into a graduated cylinder. The cone is submerged into a basin of water, forcing the lather into the cylinder. The level to which the lather fills the cylinder is taken as the volume.

Using the above-identified test, lather volumes were averaged over an average of 6 testers and the results are set forth below.

| Bar | Lather Volume |
|---|---|
| Example 19 | 120.0 ml. |
| Example 20 | 117.5 ml. |
| anionic based, free-fatty acid structured bar | 120.0 ml. |

The data above clearly illustrates that the aldobionamide bars of the invention, structured with polyalkylene glycol (15% or greater polyalkylene glycol), perform comparably to a typical anionic bar. Thus, the benefit of mild surfactants can be achieved (by using a nonionic aldobionamide) while structuring the bar and without sacrificing lather formation.

We claim:

1. A toilet bar composition comprising;
   (a) 20 to 75% by weight on a nonionic aldonamide surfactant; and
   (b) about 25 to 50% by weight polyalkylene glycol;
   wherein said toilet bar composition contains no more than 15% free fatty acid; and wherein said at least about 25% polyalkylene glycol is an amount sufficient to structure the toilet bar composition.

2. A toilet bar composition according to claim 1, wherein the aldobionamide is a lactobionamide.

3. A composition according to claim 1, wherein the polyalkylene glycol has a molecular weight of between 1,000 and 20,000.

4. A composition according to claim 3, wherein the polyalkylene glycol is polyethylene glycol.

5. A composition according to claim 1, comprising 30–60% by weight aldobionamide.

6. A composition according to claim 1, additionally comprising soap or a non-soap surfactant selected from the group consisting of anionic, nonionic, cationic, zwitterionic and amphoteric surfactants in an amount such that the additional soap or non-soap surfactant comprises no more than the amount of aldobionamide used in the composition.

7. A composition according to claim 6, wherein the soap or non-soap surfactant comprises 15–45% of the amount of aldobionamide used.

8. A toilet bar composition comprising
   (a) 30 to 60% by wt. aldobionamide; and
   (b) 25 to 50% polyalkylene glycol;
   wherein said toilet bar composition comprises no more than 15% free fatty acid; and
   wherein said polyalkylene glycol is an amount sufficient to structure the toilet bar composition.

* * * * *